United States Patent [19]
Dionne et al.

[11] Patent Number: 5,985,877
[45] Date of Patent: Nov. 16, 1999

[54] COMBINATION OF TYROSINE KINASE INHIBITOR AND CHEMICAL CASTRATION TO TREAT PROSTATE CANCER

[75] Inventors: Craig A. Dionne, Downington, Pa.; John Isaacs, Phoenix, Md.; Jeffry L. Vaught, Glenmoore, Pa.

[73] Assignee: Cephalon, Inc., West Chester, Pa.

[21] Appl. No.: 09/133,567

[22] Filed: Aug. 13, 1998

Related U.S. Application Data

[60] Provisional application No. 60/055,891, Aug. 15, 1997.

[51] Int. Cl.$^6$ ............................ A61K 45/06; A61K 31/55
[52] U.S. Cl. .............................. 514/250; 514/2; 514/16; 514/17; 514/170; 514/171; 514/211; 514/249; 514/279; 514/338; 514/339; 514/410
[58] Field of Search .................................. 514/2, 16, 17, 514/170, 171, 211, 249, 250, 279, 338, 339, 410

[56] References Cited

U.S. PATENT DOCUMENTS

| | | | |
|---|---|---|---|
| 4,659,695 | 4/1987 | Labrie | 514/15 |
| 4,923,986 | 5/1990 | Murakata et al. | 540/545 |
| 5,461,146 | 10/1995 | Lewis et al. | 540/545 |
| 5,475,110 | 12/1995 | Hudkins et al. | 546/256 |
| 5,516,771 | 5/1996 | Dionne et al. | 514/211 |
| 5,591,855 | 1/1997 | Hudkins et al. | 546/256 |
| 5,594,009 | 1/1997 | Hudkins et al. | 514/338 |
| 5,650,407 | 7/1997 | Mallamo et al. | 514/185 |
| 5,654,427 | 8/1997 | Dionne et al. | 540/545 |
| 5,659,407 | 8/1997 | Andersen et al. | 358/530 |
| 5,789,427 | 8/1998 | Chen et al. | 514/352 |

FOREIGN PATENT DOCUMENTS

WO 96/11933  4/1996  WIPO .......................... C07D 487/04

OTHER PUBLICATIONS

George et al., "Combined Effects of the Trk Tyrosine Kinase Inhibitor, EP–751 (KT–6587), and Castration on . . . ", Proceedings of American Assoc for Cancer Res. Annual Meeting, 39:664 XP002092523, 1998.

Dionne et al., "Inhibition of Prostate Tumor Growth by the Trk–selective Tyrosine Kinase Inhibitor, CEP–751 (KT–6587)", Proceedings of American Assoc. for Cancer Research Annual Meeting 38:634 XP002092524, 1997.

Lavelle, "Tyrosine Protein Kinase Inhibitors in Oncology: The End of the Beginning?", Bull. Cancer 84:769–770, 1997, Translation.

Camoratto et al., "CEP–751 Inhibits TRK Receptor Tyrosine Kinase Activity In Vitro and Exhibits and Anti–Tumor Activity", Int. J. Cancer 72:673–679, 1997.

Crawford et al., "A Controlled Trial of Leuprolide With and Without Flutamide in Prostatic Carcinoma", The New England Journal of Medicine 321:419–424, 1989.

Dionne et al., "Cell Cycle–independent Death of Prostate Aenocarcinoma is Induced by the trk Tyrosine Kinase Inhibitor CEP–751 (KT6587)", Clinical Cancer Research 4:1887–1898, 1998.

Isaacs et al., "Adaptation versus Selection as the Mechanism Responsible for the Relapse of Prostatic Cancer to Androgen Ablation Therapy as Studied in the Dunning R–3327–H . . . ", Cancer Res. 41:5070–5075, 1981.

Isaacs, "Relationship between Tumor Size and Curability of Prostatic Cancer by Combined Chemo–Hormonal Therapy in Rats", Cancer Research 49:6290–6294, 1989.

Parker et al., "Cancer Statistics, 1996", CA Cancer J. Clin. 65:5–27, 1996.

Tapley et al., "K252a is a Selective Inhibitor of the Tryosine Protein Kinase Activity of the trk Family of Oncogenes and Neurotropin Receptors", Oncogene 7:371–381, 1992.

Zaccheo et al., "Effect of Turosteride, a 5a–Reductase Inhibitor, on the Dunning R3327 Rat Prostatic Carcinoma", The Prostate 30:85–91, 1997.

*Primary Examiner*—Frederick Krass
*Attorney, Agent, or Firm*—Woodcock Washburn Kurtz Mackiewicz & Norris LLP

[57] ABSTRACT

A method of treating prostate cancer by co-administering a tyrosine kinase inhibitor such as an indolocarbazole and a chemical castration agent is disclosed. A composition containing a tyrosine kinase inhibitor and a chemical castration agent is also disclosed.

36 Claims, 4 Drawing Sheets

COMBINATION OF TYROSINE KINASE INHIBITOR AND CHEMICAL CASTRATION TO TREAT PROSTATE CANCER

CROSS REFERENCE TO RELATED APPLICATION

This application claims benefit from provisional application Ser. No. 60/055,891, filed Aug. 15, 1997.

BACKGROUND OF THE INVENTION

The invention relates to oncology, endocrinology, andrology, and pharmacology.

Prostate cancer is the most frequently diagnosed cancer in men and is responsible for approximately 41,000 deaths in the United States annually (Parker, S. L., et al. (1996) *CA Cancer J. Clin.*, 65:5–27). Early stage, organ-confined, prostate cancer is often managed with surgery or radiation therapy until the patient dies from unrelated causes.

Carcinomas such as breast cancer, colon cancer and adenocarcinoma are characterized by rapid cell division. Consequently, these cancers are amenable to treatment with chemotherapeutic agents that inhibit rapid cell division. In contrast, prostate cancer is not characterized by rapid cell division. Therefore, conventional chemotherapeutic agents generally display low efficacy against prostatic carcinomas.

Prostatic carcinomas are often sensitive to hormonal manipulation. Currently approved treatment of prostate cancer includes surgical castration, chemical castration, or a combination of surgical and chemical castration. Removal of the testes, the primary testosterone producing organ, reduces the levels of circulating androgens, to less than 5% of normal levels. This reduction in androgen levels inhibits prostate tumor growth. Although the anti-tumor effects of surgical castration are direct, the anti-tumor effects can be temporary. Surgical castration often leads to clonal selection of androgen-independent prostate tumor cells. This results in re-growth of the prostate tumor in a form that proliferates without testosterone or DHT stimulation (Isaacs et al. (1981) *Cancer Res.* 41:5070–5075; Crawford et al. (1989) *N. Eng. J. Med.* 321:419–424).

Chemical castration (also called medical castration) is often substituted for surgical castration, as an initial treatment. Chemical castration can be achieved by administration of estrogens, e.g., diethylstilbestrol (DES); LHRH analogues, e.g., leuprolide acetate (LUPRON®) or goserelin acetate (ZOLADEX®); steroidal antiandrogens, e.g., cyproterone acetate (CPA); nonsteroidal antiandrogens, e.g., flutamide, nilutamide, or CASODEX®; or a combination of such agents.

Receptor-linked tyrosine kinases are transmembrane proteins that contain an extracellular ligand binding domain, a transmembrane sequence, and a cytoplasmic tyrosine kinase domain. Tyrosine kinases function in cellular signal transduction. Cell proliferation, differentiation, migration, metabolism and programmed death are examples of tyrosine kinase-mediated cellular responses.

Tyrosine kinases have been implicated in prostate epithelial cell transformation and tumor progression. Implicated tyrosine kinases include Fibroblast Growth Factor (FGF) receptors, Epidermal Growth Factor (EGF) receptors, and Platelet-Derived Growth Factor (PDGF) receptors. Also implicated are Nerve Growth Factor (NGF) receptors, Brain-Derived Neurotrophic Factor (BDNF) receptors, and Neurotrophin-3 (NT-3) receptors, and Neurotrophin-4 (NT-4) receptors.

U.S. Pat. Nos. 5,516,771, 5,654,427 and 5,650,407 discuss indolocarbazole-type tyrosine kinase inhibitors and prostate cancer. U.S. Pat. Nos. 5,475,110; 5,591,855; and 5,594,009; and WO 96/11933 discuss fused pyrrolocarbazole-type tyrosine kinase inhibitors and prostate cancer.

SUMMARY OF THE INVENTION

It has been discovered unexpectedly that tyrosine kinase inhibitors exert their anti-tumor effects against mammalian prostate cancer by a hormone-independent mechanism. It has been further discovered that the combination of tyrosine kinase inhibitor therapy and antihormone therapy can be synergistic.

Based on these discoveries, the invention features a method for treating prostate cancer in a mammal, e.g., a human. The method includes administering a therapeutically effective amount of a tyrosine kinase inhibitor to the mammal, and co-administering a chemical castration agent to the mammal. The tyrosine kinase inhibitor and the chemical castration agent can inhibit prostate tumor progression synergistically. Preferred tyrosine kinase inhibitors include indolocarbazoles. Preferred indolocarbazoles include the following compounds:

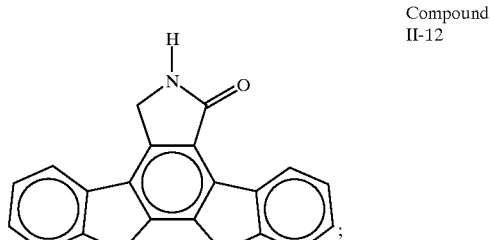

Compound II-12

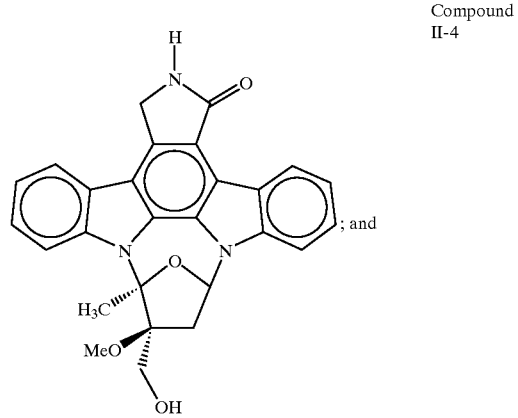

Compound II-4

-continued

Compound II-4-LAE

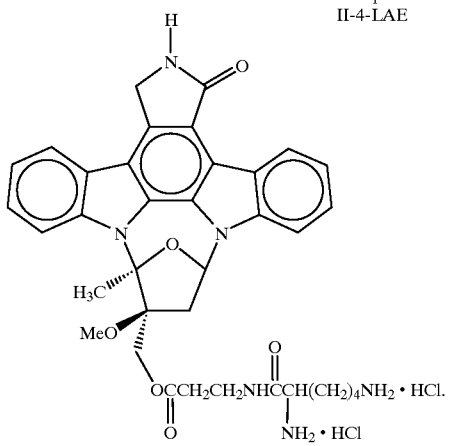

Compound II-4-LAE is the lysyl-β-alaninate ester of Compound II-4, or a pharmacologically acceptable salt of the ester, e.g., the dihydrochloride salt. Compound II-12 is described in U.S. Pat. No. 4,923,986 ("Compound 20"). Compound II-4 is described in U.S. Pat. No. 5,461,146. Compound II-4-LAE is described in U.S. Pat. No. 5,650,407 (Example 14). The tyrosine kinase inhibitor also can be be a fused pyrrolocarbazole. The tyrosine kinase inhibitor can be administered by any suitable route, e.g., orally or parenterally.

Chemical castration agents useful in the invention include estrogens; LHRH agonists, e.g., leuprolide acetate (LUPRON®) and goserelin acetate (ZOLADEX®); LHRH antagonists, e.g., ANTIDE® (Ares-Serono) and GANIRE-LIX® (Akzo Nobel); and antiandrogens, e.g., flutamide and nilutamide.

The tyrosine kinase inhibitor and the chemical castration agent can be administered in separate formulations. Alternatively, they can be formulated together and administered in a single composition.

The invention also features a composition comprising a tyrosine kinase inhibitor and a chemical castration agent. Preferably, the tyrosine kinase inhibitor in the composition is a trkA inhibitor, a trkB inhibitor, or a trkC inhibitor. Preferably, the tyrosine kinase inhibitor in the compositioin is an indolocarbazole. Preferred indolocarbazoles are (Compound II-12)

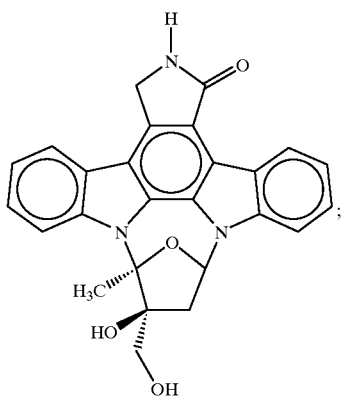

-continued (Compound II-4)

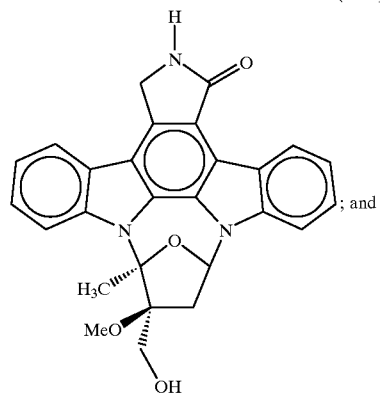

; and (Compound II-4-LAE)

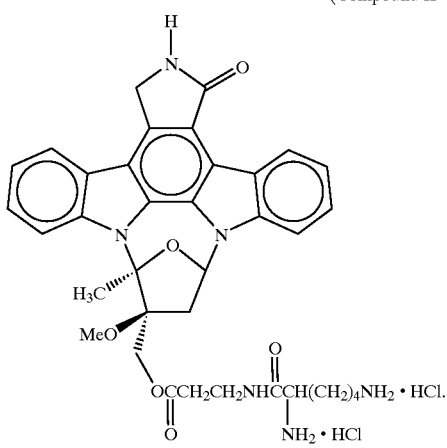

Alternatively, the tyrosine kinase inhibitor in the composition can be a fused pyrrolocarbazole. The composition can be formulated for oral administration or parenteral administration. The chemical castration agent can be an estrogen, an LHRH analog, or an antiandrogen, or a combination of two or more such compounds. A preferred LHRH analog for inclusion in the composition is leuprolide acetate. A preferred antiandrogen for inclusion in the composition is flutamide. The chemical castration agent included in the composition can be a combination of an LHRH analog and an antiandrogen, for example, leuprolide acetate and flutamide.

As used herein, "chemical castration agent" means a compound that: (1) inhibits the production of serum androgens, (2) blocks binding of serum androgens to androgen receptors, or (3) inhibits the conversion of testosterone to DHT, or a combination of two or more such compounds.

Unless otherwise defined, all technical and scientific terms used herein have the same meaning as commonly understood by one of ordinary skill in the art to which this invention belongs. In case of conflict, the present application, including definitions will control. All publications, patent applications, patents, and other references mentioned herein are incorporated by reference.

Although methods and materials similar or equivalent to those described herein can be used in the practice or testing of the present invention, the preferred methods and materials are described below. The materials, methods, and examples are illustrative only and not intended to be limiting. Other features and advantages of the invention will be apparent from the detailed description, and from the claims.

DETAILED DESCRIPTION

Figure 1:
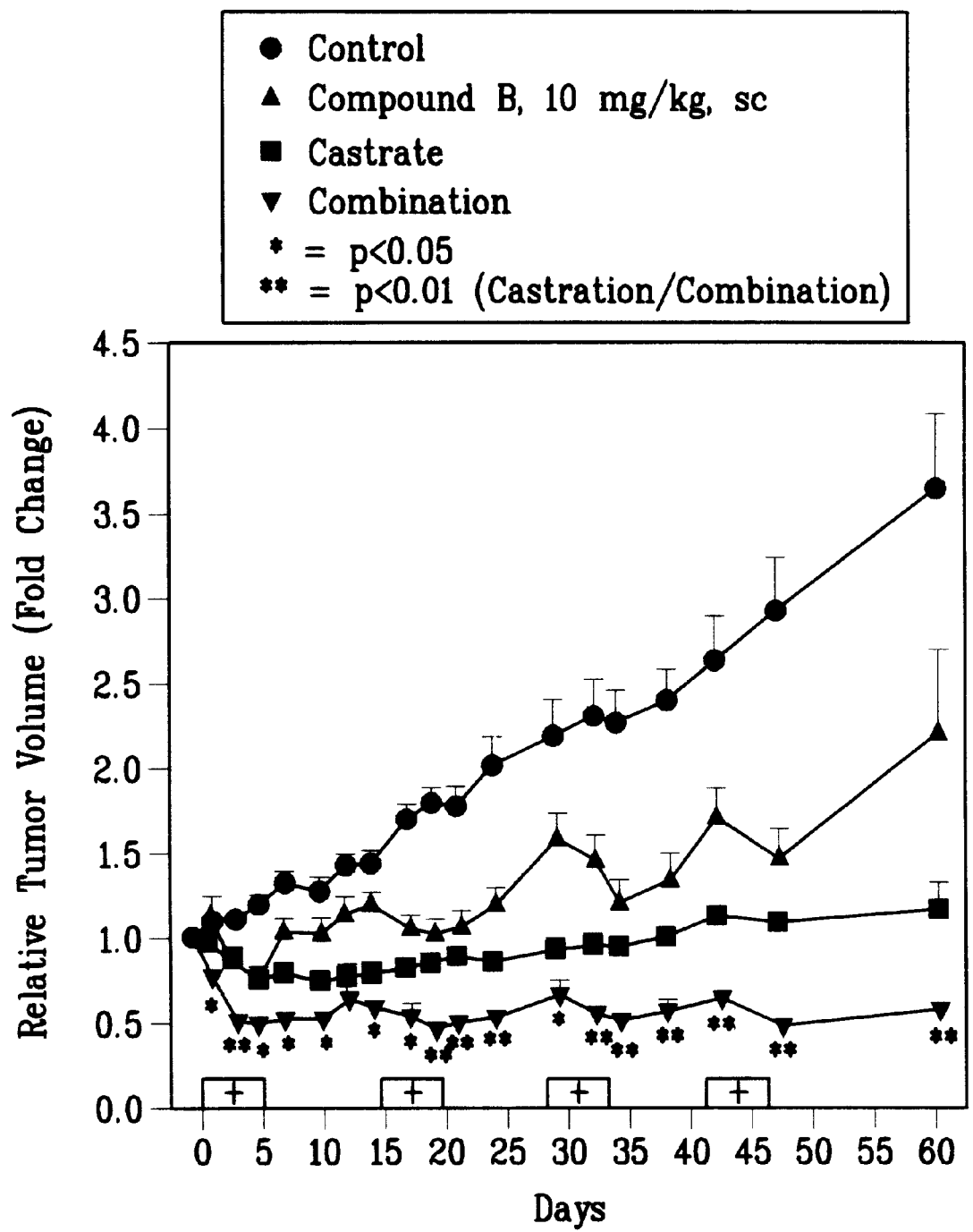
FIG. 1 is a graph of relative tumor volume (fold change) versus time (days) in an in vivo rat prostate tumor model system. Circles, vehicle control; upright triangles, Compound II-4 monotherapy control; squares, castrate controls; inverted triangles, Compound II-4/castration combination treatment. Compound II-4 dosage was 10 mg/kg, by subcutaneous injection. Compound II-4 administration is indicated by rectangles containing plus signs on the X axis.

The co-administration of a tyrosine kinase inhibitor and a chemical castration agent can be by concurrent administration of separate formulations, i.e., a tyrosine kinase formulation and a chemical castration agent formulation. Administration of separate formulations is "concurrent" if the timing of their administration is such that the pharmacological activities of the tyrosine kinase inhibitor and the chemical castration agent occur simultaneously in the mammal undergoing treatment.

In some embodiments of the invention, co-administration of a tyrosine kinase inhibitor and a chemical castration agent is accomplished by formulating them into a single composition.

Preferably, the dosage of the tyrosine kinase inhibitor is from 1 µg/kg to 1 g/kg of body weight per day. More preferably, the dosage of the tyrosine kinase inhibitor is from 0.01 mg/kg to 100 mg/kg of body weight per day. The optimal dosage of the tyrosine kinase inhibitor will vary, depending on factors such as type and extent of progression of the prostate cancer, the overall health status of the patient, the potency of the tyrosine kinase inhibitor, and route of administration. Optimization of the tyrosine kinase dosage is within ordinary skill in the art.

Various tyrosine kinase inhibitors suitable for use in this invention are known in the art. Preferably, the tyrosine kinase inhibitor used in this invention is a trk A inhibitor, a trk B inhibitor, or a trk C inhibitor. Suitable indolocarbazole-type tyrosine kinase inhibitors can be obtained using information found in documents such as Dionne et al., U.S. Pat. No. 5,516,771, Dionne et al., U.S. Pat. No. 5,654,427, Lewis et al., U.S. Pat. No. 5,461,146, and Mallamo et al., U.S. Pat. No. 5,650,407.

In some embodiments of the invention, Compound II-4-LAE is prepared and administered to a human patient according to the following procedure. Compound II-4-LAE (dihydrochloride) and an osmotically suitable amount of mannitol are dissolved in distilled water, and the pH is adjusted to approximately 3.5. This solution is lyophilized to produce a powder. For storage and convenient use, aliquots of the lyophilized powder containing 27.5 mg of Compound II-4-LAE and 55 mg of mannitol are prepared. At the time of use, an aliquot of lyophilized powder is redissolved in sterile water for injection, USP, to yield 1.1 ml containing 50 mg/ml mannitol and 25 mg/ml of Compound II-4-LAE (dihydrochloride). This reconstituted solution is then diluted with an appropriate volume of 5% Dextrose Injection, USP, for administration of the desired Compound II-4-LAE dose by intravenous infusion over a period of approximately one hour. The dosage of Compound II-4-LAE in this procedure can be conveniently initiated at 1 mg/meter$^2$/day and gradually increased, for example to 64 mg/meter$^2$/day, or 501 mg/meter$^2$/day, as the patient's progress is monitored.

Various chemical castration agents are known. Known chemical castration agents useful in this invention are sometimes categorized as follows: estrogens, leuteinizing hormone-releasing hormone (LHRH) agonists, LHRH antagonists, and antiandrogens. Antiandrogens can be further categorized as steroidal or nonsteroidal.

Estrogens, e.g., diethylstilbestrol (DES), raise sex hormone-binding globulin levels and plasma prolactin levels. This reduces LH secretion and testicular testosterone synthesis through a negative feedback response. Dosage of DES is often from 1 mg/day to 5 mg/day. Preferably, higher dosages of DES are avoided because of possible complications relating to cardiovascular risk.

An LHRH agonist preferred for use in this invention is leuprolide acetate, commercially available as LUPRON® (Takeda Abbott Pharmaceuticals, Inc.). The chemical name of leuprolide acetate is 5-oxo-L-prolyl-L-histidyl-L-tryptophyl-L-seryl-L-tyrosyl-D-leucyl-L-leucyl-L-arginyl-N-ethyl-L-prolinamide acetate (salt). Leuprolide acetate, an LHRH agonist, is a potent inhibitor of gonadotropin secretion when administered continuously and in therapeutic doses. This effect is reversible upon discontinuation of leuprolide acetate administration.

Leuprolide acetate, e.g., LUPRON DEPOT®, is believed to act by a negative feedback mechanism. In humans, subcutaneous administration of single daily doses of leuprolide acetate causes an initial increase in serum levels of leuteining hormone (LH). In males, within two to four weeks after initiation of leuprolide acetate administration, serum testosterone falls to castrate levels.

When used in this invention, leuprolide acetate is administered subcutaneously, intramuscularly, or intravenously. Leuprolide acetate can be administered, for example, by subcutaneous injection of 1 mg per day. In some embodiments of the invention, leuprolide acetate is administered in a depot formulation. A depot formulation conveniently provides sustained release of the drug over an extended time period, e.g., 1 to 4 months. An exemplary depot formulation includes a suspension of microspheres containing leuprolide acetate, purified gelatin, DL-lactic and glycolic acids copolymer, and D-mannitol. The microspheres can be suspended in a carrier containing carboxymethylcellulose sodium, D-mannitol, and water. Such a depot formulation is commercially available as LUPRON DEPOT™ (Takeda Abbott Pharmaceuticals) and is suitable for intramuscular injection.

Another LHRH agonist useful in this invention is goserelin acetate, commercially available as ZOLADEX® (Zeneca). The chemical structure of goserelin acetate is pyro-Glu-His-Trp-Ser-Tyr-D-Ser(Bu$^t$)-Leu-Arg-Pro-Azgly-NH$_2$ acetate. ZOLADEX® is supplied as a formulation designed for subcutaneous injection with continuous release over a 28-day period.

An example of an LHRH antagonist useful in this invention is ANTIDE® (Ares-Serono), whose chemical name is D-alaninamide N-acetyl-3-(2-naphthalenyl)-D-alanyl-4-chloro-D-phenylalanyl-3-(3-pyridinyl)-D-alanyl-L-seryl-N6-(3-pyridinylcarbonyl)-L-lysyl-N6-(3-pyridinylcarbonyl)-D-lysyl-L-leucyl-N6-(1-methylethyl)-L-lysyl-L-prolyl. Another example of a useful LHRH antagonist is GANIRELIX® (Roche/Akzo Nobel), whose chemical name is N-Ac-D-Nal,D-pCl-Phe,D-Pal,D-hArg(Et)2,hArg(Et)2,D-Ala.

Examples of steroidal antiandrogens are cyproterone acetate (CPA) and megestrol acetate, commercially available as MEGACE® (Bristol-Myers Oncology). Steroidal antiandrogens may block prostatic androgen receptors. They may also inhibit the releast of LH. CPA is preferably administered to human patients at dosages of 100 mg/day to 250 mg/day.

Nonsteroidal antiandrogens block androgen receptors. They may also cause an increase in serum LH levels and serum testosterone levels. A preferred nonsteroidal antiandrogen is flutamide (2-methyl-N-[4-nitro-3-(trifluoromethyl)phenyl] propanamide), commercially available as EULEXIN® (Schering Corp.). Flutamide exerts is antiandrogenic action by inhibiting androgen uptake, by inhibiting nuclear binding of androgen in target tissues, or both. Flutamide is typically administered orally, e.g., in capsule form. An exemplary flutamide dosage is 250 mg, three times per day, i.e., 750 mg per day.

Another nonsteroidal antiandrogen is nilutamide, whose chemical name is 5,5-dimethyl-3-[4-nitro-3-(trifluoromethyl-4'-nitrophenyl)-4,4-dimethylimidazolidine-dione. When used in this invention, an exemplary dosage of nilutamide 300 mg daily, followed by a reduced dosage of 150 mg/day.

In some embodiments of the invention, the chemical castration agent is a combination of an LHRH agonist such as leuprolide acetate, and an antiandrogen such as flutamide or nilutamide. For example, leuprolide acetate can be administered by subcutaneous, intramuscular or intravenous injection, and concurrently the flutamide can be administered orally. The tyrosine kinase inhibitor can be administered separately in a third formulation, or it can be formulated together with the LHRH agonist or the antiandrogen.

Another nonsteroid antiandrogen useful in this invention is CASODEX®. An exemplary dosage of CASODEX® is from 5 mg to 500 mg per day, preferably about 50 mg per day.

An exemplary combined formulation according to this invention includes 1–20 mg of Compound II-12 and 100–1000 mg of flutamide in a capsule for oral administration to a human patient, once, twice, or three times per day. In a preferred embodiment, the formulation includes a vehicle containing polysorbate 80 and polyethylene glycol in a ratio of 1:1 (v/v), to enhance bioavailability of Compound II-12. In some embodiments, this Compound II-12/ flutamide oral formulation is supplemented by an intramuscular injection of a leuprolide acetate depot injection, e.g., LUPRON DEPOT®. Another tyrosine kinase such as Compound II-4 or Compound II-4-LAE can be substituted for Compound II-12 in this formulation. Other exemplary combined formulations according to this invention include Compound II-12, Compound II-4 or Compound II-4-LAE, and a chemical castration agent, in a single solution suitable for intravenous infusion.

Tyrosine kinase inhibitors and chemical castration agents can be formulated, individually or in combination, into pharmaceutical compositions by admixture with pharmaceutically acceptable nontoxic exipients and carriers. Such compositions can be prepared for use in parenteral administration, particularly in the form of liquid solutions or suspensions; for oral administration, particularly in the form of liquid, tablets or capsules; or intranasally, particularly in the form of powders, nasal drops, or aerosols.

The composition can be administered conveniently in unit dosage form and can be prepared by any of the methods known in the art. Such methods are described, for example, in *Remington's Pharmaceutical Sciences* (Mack Pub. Co., Easton, Pa., 1980).

Liquid dosage forms for oral administration include pharmaceutically acceptable emulsions, microemulsions, solutions, suspensions, syrups and elixirs. In addition to the active compound, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable depot forms are made by forming microencapusule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, 3) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. In solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The invention is further illustrated by the following examples. The examples are provided for illustration purposes only, and they are not to be construed as limiting the scope or content of the invention in any way.

EXAMPLES

Example 1

Compound II-4 Combined with Surgical Castration

Data from animal experiments involving tyrosine kinase administration in combination with surgical castration were considered relevant to tyrosine kinase administration in combination with chemical castration.

The Dunning R-3327 H tumor (derived from a spontaneous prostate tumor in an aged Copenhagen rat) was used in these experiments because of its androgen-sensitivity and its slow growth rate (Isaacs, 1989, *Cancer Res.* 49:6290–6294). A consideration in the experimental design was that surgical castration of rats harboring Dunning H tumors leads to almost immediate cessation of tumor growth followed by androgen-insensitive tumor regression at about 5–6 weeks post-castration (Isaacs et al. (1981) *Cancer Res.* 41:5070–5075).

The Dunning H tumor regression induced by Compound II-4 was not due to an effect on androgen levels, because the experiments were performed in rats implanted with testosterone-releasing silastic capsules. The implanted capsules were designed to maintain circulating testosterone at physiological levels. Serum testosterone levels measured at the end of the experiment confirmed that testosterone was $\geq 1-2$ ng/ml.

The following experiment had three objectives: 1) to determine whether the combination of Compound II-4 with surgical castration would provide greater anti-tumor efficacy than Compound II-4 or surgical castration alone; 2) to determine whether Compound II-4 could cause regression of Dunning H tumors that had been selected hormone insensitivity by prior castration of the host animals; and 3) to determine if tumors treated with Compound II-4 for several dosing cycles were still sensitive to surgical castration.

Compound II-4 was synthesized at Cephalon, Inc. and formulated (10 mg/ml) in a vehicle containing 40% polyethylene glycol (PEG 1000, Spectrum, Los Angeles, Calif.), 10% polyvinylpyrrolidone (C30, ISP Boundbrook, N.J.), 2% benzyl alcohol (Spectrum, Los Angeles, Calif.) in water (48%).

Adult, male, inbred Copenhagen rats (200–240 g) obtained from Harlan Sprague Dawley (Indianapolis, Ind.) were maintained three rats/cage and give a commercial diet (Purina Formulab 5001) and water ad libitum. Animals were housed under humidity-controlled, temperature-controlled conditions, with a light/dark cycle of 12-hour intervals. Rats were quarantined for one week before experimental manipulation. Rat prostate cancer Dunning R-3327 H tumors were transplanted using trocar pieces. An adult male Copenhagen rat bearing a Dunning H tumor was sacrificed and the tumor was isolated. The tumor was cut, and small pieces were inoculated subcutaneously in adult, male Copenhagen rats.

Experiments were performed under the guidelines of the Johns Hopkins University Animal Care and Use Committee Protocol No. RA91M517 and the Cephalon Institutional Animal Care and Use Committee Protocol No. 03-008.

For surgical castration, rats bearing established Dunning H tumors were anesthetized by intramuscular injection of KETAMINE™ (4.1 mg/100 g body weight) and XYLAZINE™ (0.85 mg/100 g body weight). Each rat was placed on its back. A small incision (0.5–1 cm) was made through the skin at the posterior tip of the scrotum. Another incision was made to break the connective membrane surrounding the testes. The epididymis, testes, vas deferens, the spermatic blood vessels, and the fat were pulled out and severed. Any remaining tissues were pushed back into the sac, and the incision was closed with autoclips. The autoclips were removed 5–7 days following surgery.

Thirty six Dunning H tumor-bearing rats (0.9–18 cm$^3$ in size) were divided into four groups of nine animals each. Group 1 served as a vehicle control. Group 2 was castrated on Day 1. Group 3 received injections of Compound II-4 (10 mg/kg, sc) as described below. Group 4 was castrated on Day 1 and given injections of Compound II-4 as described below. Groups 1 and 3 were implanted subcutaneously (in the flank) with a 2 cm long sealed silastic tube filled with testosterone on Day 1. A silastic implant of this size was suitable to maintain serum testosterone in the physiological range of 1–3 ng/ml chronically for a duration of six months. Compound II-4 was administered sub-cutaneously (10 mg/kg/day) to Groups 3 and 4 on a periodic, 5-day dosing cycle with approximately 10 days between cycles. The drug was administered on Days 1–5, 14–18, 29–33 and 42–46. The drug vehicle was administered to Groups 1 and 2 on the same schedule as the Compound II-4-treated groups.

Eight rats from Group 2 were divided into two groups of four rats each on Day 60. One group was treated with Compound II-4, 10 mg/kg, (subcutaneous) for 5 days, followed by drug withdrawal for 9 days, followed by a second five-day dosing regime at 10 mg/kg/day (subcutaneous). The second group received vehicle on the same dosing schedule.

Seven rats derived from Group 3 of the preceding experiment were divided into two groups on Day 60. One group (N=3) of rats was castrated. Both groups were treated with Compound II-4, 10 mg/kg (subcutaneous) for 5 days, followed by drug withdrawal for 9 days, followed by a second five-day dosing regime as before.

Tumors were measured on anesthetized animals (isofluorane vapor for approximately 1–2 minutes) at indicated intervals using a vernier caliper. Tumor volume was calculated using the formula: $V(cm^3)=0.5236 \times length(cm) \times width(cm) [(length(cm)+width(cm))/2]$.

The Dunnett's test, Mann-Whitney Rank Sum Test, Paired t Test, or Signed Rank Test of significance was applied for statistical analysis using the SigmaStat program.

The growth of Dunning H tumors in intact, vehicle-treated rats was linear, and an approximately 3.5-fold increase in tumor volume over 60 days was observed (FIG. 1). Surgical castration caused a rapid regression of tumors, i.e., 25% by Day 5. Tumor re-growth in castrated rats was observed by Day 12, and complete recovery of the regressed tumor volume was achieved by Day 38.

Compound II-4 alone (10 mg/kg, sc; 4 independent cycles of Compound II-4 treatment: 5 days of drug treatment followed by drug withdrawal for approximately 10 days) caused complete tumor growth inhibition or induced tumor regression. The average tumor volume in drug-treated animals was significantly smaller ($p<0.01$) than in vehicle treated control animals after each cycle of Compound II-4 administration (days 5, 19, 34 and 47; data not shown). In addition, each cycle of Compound II-4 administration caused regression relative to tumor volume at the start of each dosing cycle (data not shown).

The combination of Compound II-4 with surgical castration caused complete inhibition of tumor growth or induced tumor regression (FIG. 1). Overall, the combination of Compound II-4 administration and surgical castration was significantly more effective than surgical castration alone. In vivo tumor re-growth was observed after Compound II-4 withdrawal in both castrated and non-castrated animals, However, re-growth was minimal in castrated animals ($p<0.01$, FIG. 1).

These results demonstrated that Compound II-4 can be used in combination with surgical castration to maximize degree and/or duration of regression of tumors in an accepted in vivo model of prostate cancer.

Further experiments were conducted to determine whether Compound II-4 treatment causes regression of tumors selected to be hormone insensitive via prior androgen ablation. Eight rats from the castrated group of the preceding experiment (no prior treatment with Compound II-4) were divided into two groups of four rats each on Day 60. One group was treated with Compound II-4, 10 mg/kg, sc for 5 days followed by drug withdrawal for 9 days followed by a second five-day dosing regime at 10 mg/kg/day, sc. The second group received vehicle on the same dosing schedule.

Figure 2:
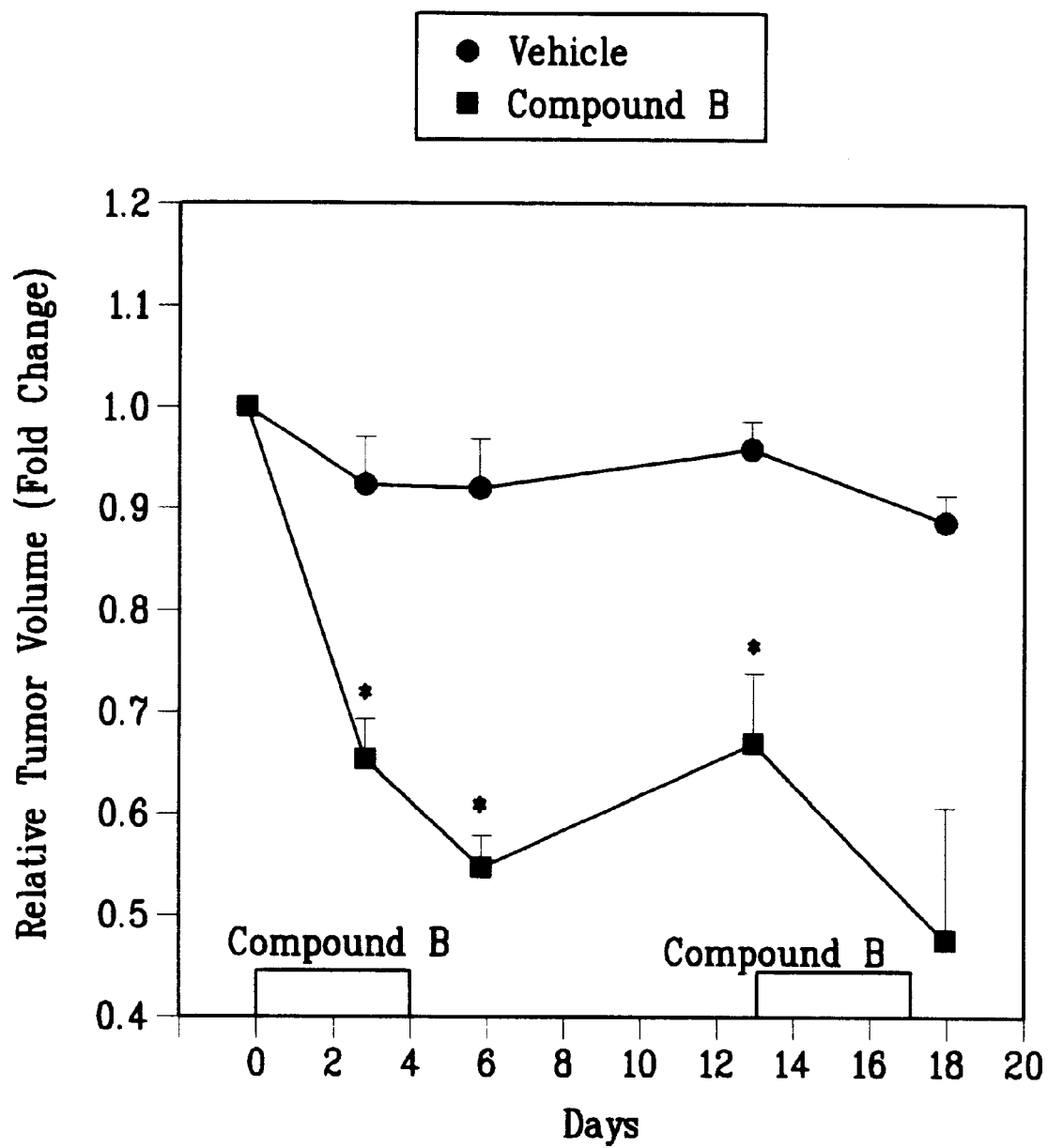
FIG. 2 is a graph of relative tumor volume (fold change in Dunning H tumors) versus time (days) in castrated rats. Circles, vehicle control; squares, Compound II-4. Time of Compound II-4 administration is indicated by rectangles on the X axis.

Treatment with Compound II-4 caused a significant regression of androgen-insensitive Dunning H tumors grown in castrated rats by Day 3 ($p<0.05$; FIG. 2). Maximal regression was observed by Day 6 ($p<0.05$). Drug withdrawal allowed the tumors to re-grow. However, the tumor volume in Compound II-4 treated rats was significantly less ($p<0.05$) than vehicle treated animals even 10 days after the end of first Compound II-4 cycle. Dunning H tumors selected to be hormone insensitive via prior androgen ablation were still sensitive to the anti-tumor action of Compound II-4.

Figure 3:
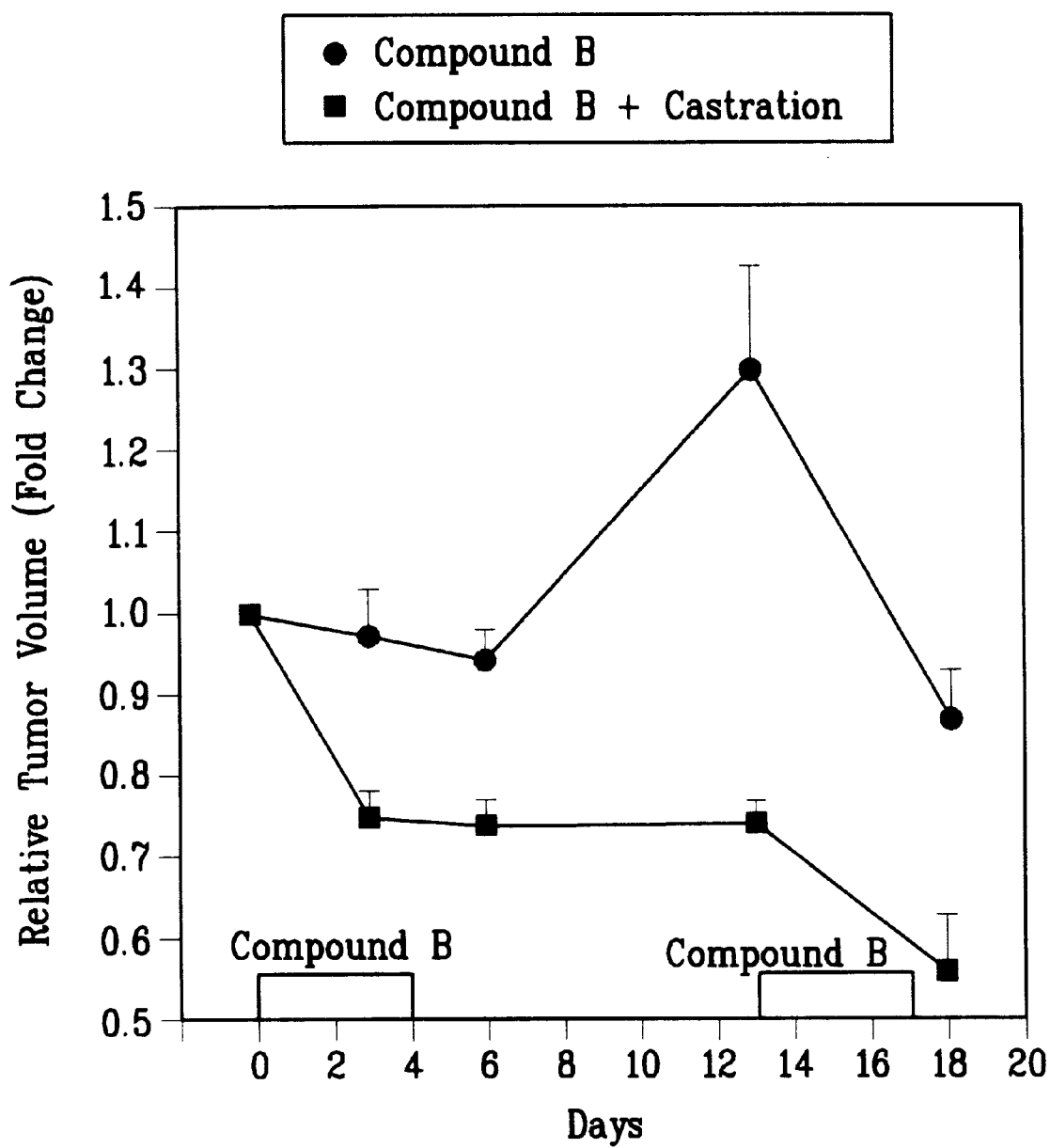
FIG. 3 is a graph of relative tumor volume (fold change) versus time (days) in rats previously treated with Compound II-4. Circles, Compound II-4; squares, Compound II-4/castration treatment. Time of Compound II-4 administration is indicated by rectangles on the X axis.

Experiments were also conducted to determine whether prior Compound II-4 treatment of rats bearing Dunning H tumors could cause selection of tumors insensitive to subsequent androgen ablation via surgical castration. Seven rats from Compound II-4 treated group of the preceding experiment were divided into two groups on Day 60. One group (N=3) was castrated as described above. Both groups were treated with Compound II-4, 10 mg/kg, sc for 5 days followed by drug withdrawal for 9 days followed by a second five day dosing regime as before. Surgical castration caused a non-statistically-significant regression of tumors that had undergone four prior cycles, and two concurrent cycles, of Compound II-4 treatment (FIG. 3). Overall, the data indicated that repeated exposure to Compound II-4 did not select an androgen-insensitive population of Dunning H tumors.

Castration, Compound II-4 treatment, and the combination of Compound II-4 with surgical castration was well tolerated. Limited mortality was observed in control and castrated groups of animals treated with vehicle or Compound II-4. In each case, mortality occurred at the time of tumor measurement, presumably due to anesthesia overdose.

EXAMPLE 2

Combination of Compound II-12 and Chemical Castration

Compound II-12 was synthesized at Cephalon, Inc. Compound II-12 dihydrochloride was formulated (10 mg/ml) in a vehicle containing 3:2 (v/v) Gelucire (Gattefosse, Saint-Priest, France) in propylene glycol (Spectrum, Gardena, Calif.)

Adult, male, inbred, Copenhagen rats (200–240 g) obtained from Harlan Sprague Dawley (Indianapolis, Ind.) were used in this experiment. Maintenance and manipulation of the rats, and transplantation of Dunning R-3327 H tumors, was as described in Example 1 (above).

Forty six rats (weight: 380±8 g) harboring Dunning H tumors ($\frac{1}{6}$–33.2 cm$^3$ in size) were divided into four groups. Group 1 (N=12) served as vehicle control (1 ml/kg, po BID, Days 0–20 and 31–45). Group 2 (N=10) was treated with leuprolide acetate (LUPRON DEPOT®) (5.2 mg/kg, sc on Days 0 and 21). Group 3 (N=12) received Compound II-12 (10 mg/kg, po BID on Days 0–20 and 31–45). Group 4 (N=12) received a combination of leuprolide acetate (5.2 mg/kg, sc on Days 0 and 21) and Compound II-12 (10 mg/kg, po BID on Days 0–20 and 31–45). Animals of groups 1 and 3 were implanted sc with a 2 cm long silastic capsule filled with testosterone.

Tumor measurements and statistical analyses were performed as described in Example 1 (above).

In vivo growth of the Dunning H tumors was consistent in vehicle-treated animals. An approximately 2.5-fold increase in tumor volume was observed by Day 53. Initiation of each Compound II-12 treatment cycle (10 mg/kg BID, po for 21 days with an interim drug free period of ten days) inhibited Dunning H tumor growth and caused marked tumor regression. Inhibition of tumor growth observed in the Compound II-12 treatment group was statistically significant, as compared with the vehicle control group. This difference was observed from the earliest tumor measurement, i.e., Day 4, until termination of the experiment). Leuprolide acetate treatment alone also resulted in tumor regression. Slow tumor re-growth was observed approximately 32 days after initiation of leuprolide treatments (FIG. 4).

Figure 4:
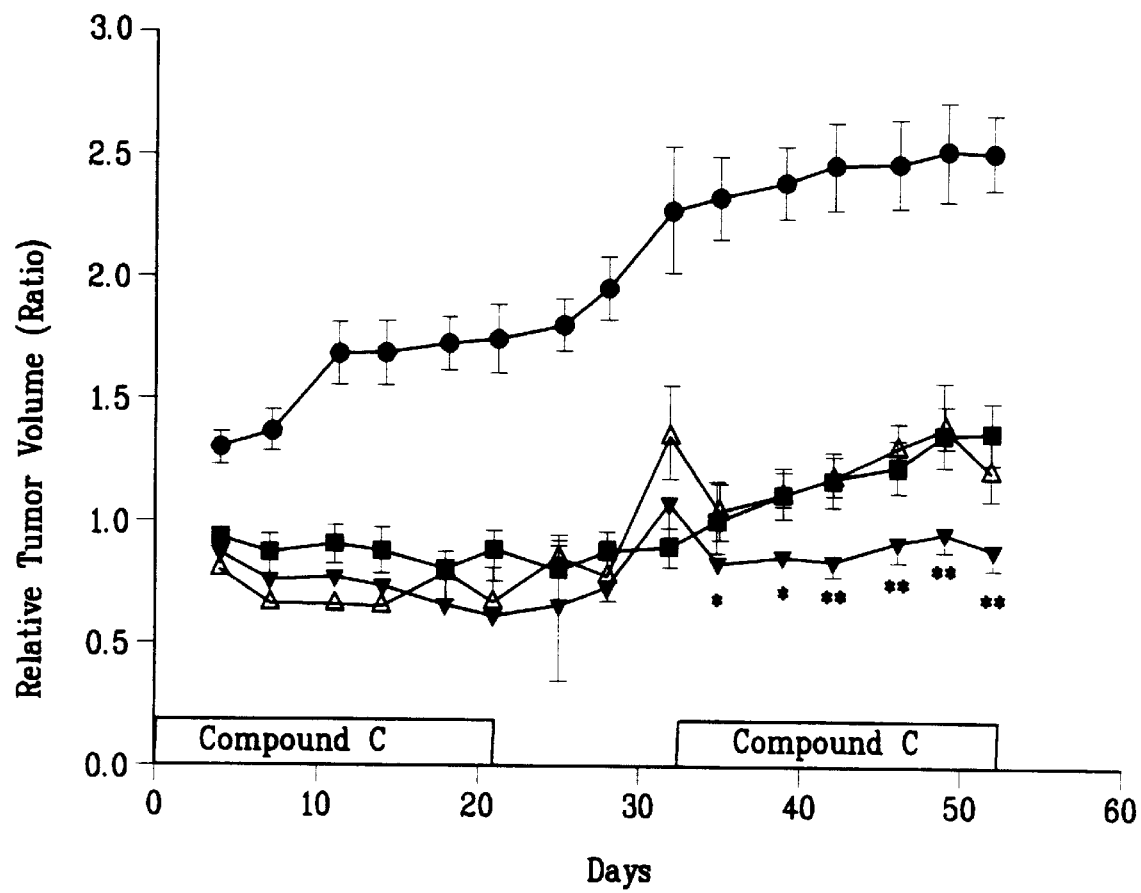
FIG. 4 is a graph of relative tumor volume (fold change) versus time (days) in an in vivo rat prostate tumor model system. Circles, vehicle control; upright triangles, Compound II-12 monotherapy control; squares, chemically castrated controls receiving leuprolide acetate (LUPRON®); inverted triangles, Compound II-12/leuprolide acetate combination treatment. Compound II-4 dosage was 10 mg/kg BID, per os. Compound II-12 administration is indicated by rectangles on the X axis.

As compared to leuprolide alone, or Compound II-12 alone, the Compound II-12/leuprolide combination was significantly more effective ($p.<0.05$) in maintaining a reduced rate of tumor growth than either treatment alone (FIG. 4). Tumor regrowth was observed in the Compound II-12 treatment group and the leuprolide treatment group, approximately thirty days after initiation of treatments. In contrast, the combination treatment group exhibited a longer duration of reduced tumor growth and was statistically different from the Compound II-12 group and the leuprolide group from days 35 and 39 respectively, until termination of the experiment on Day 54 (p.<0.05; FIG. 4).

These experimental results demonstrated that the combination Compound II-12 with chemical castration was synergistic in anti-tumor efficacy (FIGS. 1 and 4).

Other embodiments are within the following claims.

We claim:

1. A method for inhibiting prostate tumor progression in a mammal in need thereof, comprising administering a therapeutically effective amount of a tyrosine kinase inhibitor to the mammal, and co-administering a therapeutically effective amount of a chemical castration agent to the mammal, wherein the tyrosine kinase inhibitor is a trkA inhibitor, a trkB inhibitor, or a trkC inhibitor.

2. The method of claim 1, wherein the mammal is a human.

3. The method of claim 1, wherein the tyrosine kinase inhibitor is an indolocarbazole.

4. The method of claim 3, wherein the indolocarbazole has the following structure:

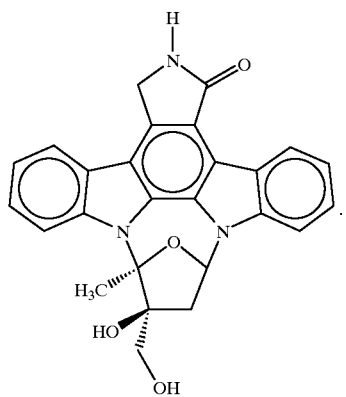

(Compound II-12)

5. The method of claim 3, wherein the indolocarbazole has the following structure:

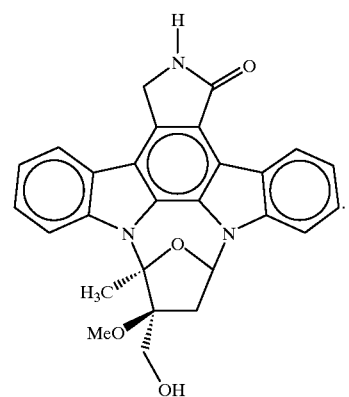

(Compound II-4)

6. The method of claim 3, wherein the indolocarbazole has the following structure:

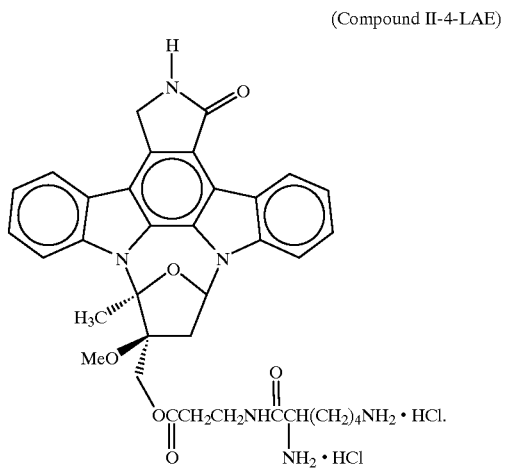

(Compound II-4-LAE)

7. The method of claim 1, wherein the tyrosine kinase inhibitor is a fused pyrrolocarbazole.

8. The method of claim 1, wherein the tyrosine kinase inhibitor is administered orally.

9. The method of claim 1, wherein the tyrosine kinase inhibitor is administered parenterally.

10. The method of claim 1, wherein the chemical castration agent is selected from the group consisting of an estrogen, an LHRH agonist, an LHRH antagonist, and an antiandrogen.

11. The method of claim 10, wherein the LHRH agonist is leuprolide acetate.

12. The method of claim 10, wherein the antiandrogen is flutamide.

13. The method of claim 1, wherein the chemical castration agent is a combination of an LHRH agonist and an antiandrogen.

14. The method of claim 13, wherein the LHRH agonist is leuprolide acetate, and the antiandrogen is flutamide.

15. The method of claim 1, wherein the tyrosine kinase inhibitor and the chemical castration agent are administered in separate formulations.

16. The method of claim 1, wherein the tyrosine kinase inhibitor and the chemical castration agent are formulated together in a single composition.

17. A composition comprising a tyrosine kinase inhibitor and a chemical castration agent, wherein the tyrosine kinase inhibitor is a trkA inhibitor, a trkB inhibitor, or a trkC inhibitor.

18. The composition of claim 17, wherein the tyrosine kinase inhibitor is an indolocarbazole.

19. The composition of claim 18, wherein the indolocarbazole is selected from the group consisting of: an indolocarbazole whose structure is:

an indolocarbazole whose structure is:

(Compound II-12)

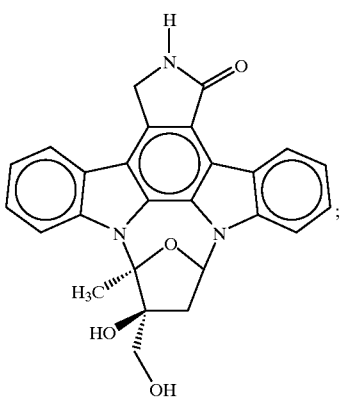

an indolocarbazole whose structure is:

(Compound II-4)

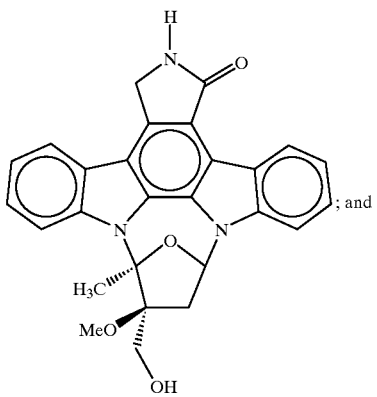
; and (Compound II-4-LAE)

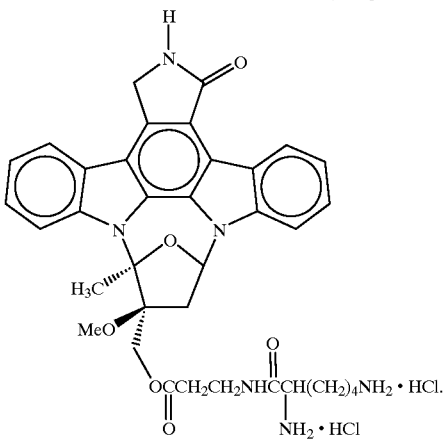

20. The composition of claim 17, wherein the tyrosine kinase inhibitor is a fused pyrrolocarbazole.

21. The composition of claim 17, wherein the composition is formulated for oral administration.

22. The composition of claim 17, wherein the composition is formulated for parenteral administration.

23. The composition of claim 17, wherein the chemical castration agent is selected from the group consisting of an estrogen, an LHRH agonist, an LHRH antagonist, and an antiandrogen.

24. The composition of claim 23, wherein the LHRH agonist is leuprolide acetate.

25. The composition of claim 23, wherein the antiandrogen is flutamide.

26. The composition of claim 17, wherein the chemical castration agent is a combination of an LHRH agonist and an antiandrogen.

27. The composition of claim 26, wherein the LHRH agonist is leuprolide acetate, and the antiandrogen is flutamide.

28. The method of claim 10, wherein the chemical castration agent is an LHRH antagonist.

29. The method of claim 28, wherein the LHRH antagonist is selected from the group consisting of:

D-alaninamide N-acetyl-3-(2-naphthalenyl)-D-alanyl-4-chloro-D-phenylalanyl-3-(3-pyridinyl)-D-alanyl-L-seryl-N6-(3-pyridinylcarbonyl)-L-lysyl-N6-(3-pyridinylcarbonyl)-D-lysyl-L-leucyl-N6-(1-methylethyl)-L-lysyl-L-prolyl, and N-Ac-D-Nal,D-pCl-Phe,D-Pal,D-hArg(Et)2,hArg(Et)2, D-Ala.

30. A method for inhibiting prostate tumor progression in a mammal in need thereof, comprising:

administering to the mammal a therapeutically effective amount of a compound whose chemical structure is:

(Compound II-12)

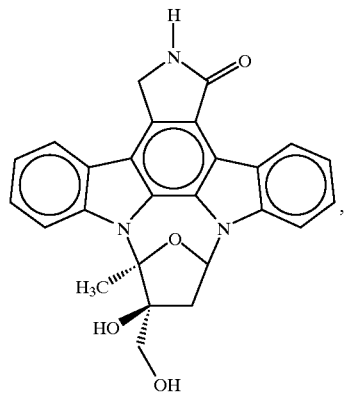

and co-administering a therapeutically effective amount of an LHRH antagonist.

31. A method for inhibiting prostate tumor progression in a mammal in need thereof, comprising:

administering to the mammal a therapeutically effective amount of a compound whose chemical structure is

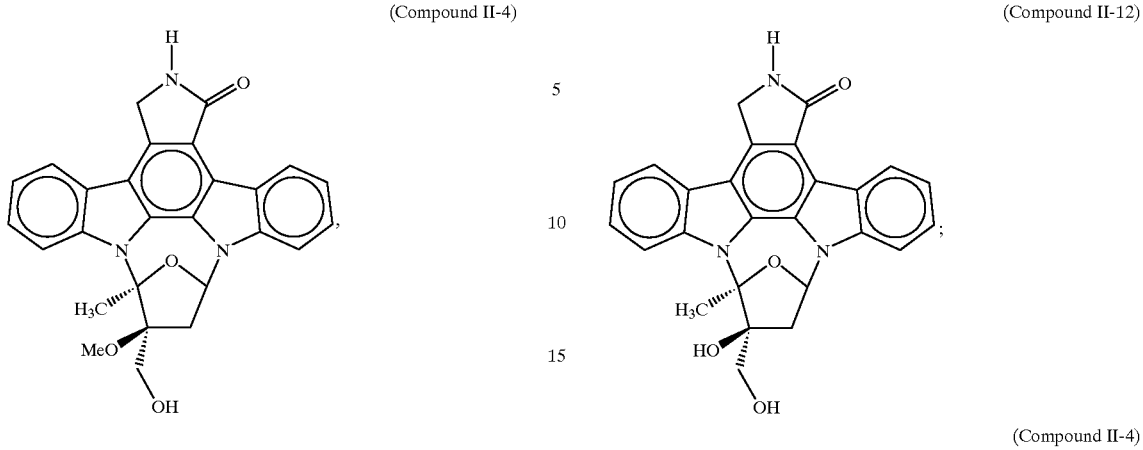

and co-administering a therapeutically effective amount of an LHRH antagonist.

32. A method for inhibiting prostate tumor progression in a mammal in need thereof, comprising:

administering to the mammal a therapeutically effective amount of a compound whose chemical structure is (Compound II-4-LAE)

and co-administering a therapeutically effective amount of an LHRH antagonist.

33. A pharmaceutical composition comprising a tyrosine kinase inhibitor and a chemical castration agent, wherein the tyrosine kinase inhibitor is a trkA inhibitor, a trkB inhibitor, or a trkC inhibitor, and a pharameutically acceptable carrier thereof.

34. A pharmaceutical composition comprising a chemical castration agent and a tyrosine kinase inhibitor which is selected from the group consisting of indolocarbazoles whose structures are:

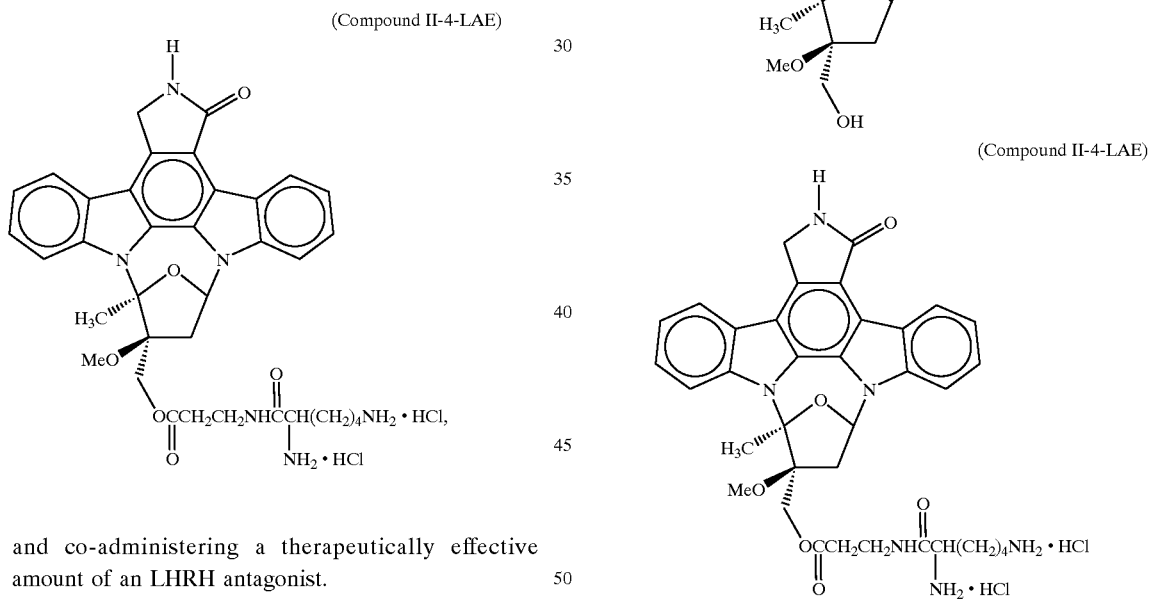

and a pharmaceutically acceptable carrier therefore.

35. The pharmaceutical composition of claim 34, wherein the chemical castration agent is selected from the group consisting of an estrogen, an LHRH agonist, an LHRH antagonist, and an antiandrogen.

36. The pharmaceutical composition of claim 35, wherein the chemical castration agent is an LHRH antagonist.

* * * * *